(12) United States Patent
Pressman et al.

(10) Patent No.: US 6,191,299 B1
(45) Date of Patent: Feb. 20, 2001

(54) METHOD FOR MAKING AROMATIC CARBONATES

(75) Inventors: Eric James Pressman, East Greenbush; Bruce Fletcher Johnson, Scotia, both of NY (US); Phillip Oscar Moreno; Richard Anthony Battista, both of Dalton, MA (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 09/224,162

(22) Filed: Dec. 31, 1998

(51) Int. Cl.$^7$ .................................................. C07C 68/00
(52) U.S. Cl. ........................ 558/274; 558/271; 558/272; 558/273
(58) Field of Search ............................................ 558/274

(56) References Cited

U.S. PATENT DOCUMENTS

| | | |
|---|---|---|
| 4,187,242 | 2/1980 | Chalk . |
| 5,142,086 | 8/1992 | King, Jr. et al. . |
| 5,231,210 | 7/1993 | Joyce et al. . |
| 5,284,964 | 2/1994 | Pressman et al. . |
| 5,336,803 | 8/1994 | Kezuka et al. . |
| 5,498,789 | 3/1996 | Takagi et al. . |
| 5,502,232 | * 3/1996 | Buysch et al. ............... 558/274 X |
| 5,898,079 | * 4/1999 | Pressman et al. ............... 558/274 |

FOREIGN PATENT DOCUMENTS

| | | |
|---|---|---|
| 350697A3 | 1/1990 | (EP) . |
| 350700A3 | 1/1990 | (EP) . |
| 0 633 388 A1 | 7/1995 | (EP) . |
| 0 858 991 A1 | 8/1998 | (EP) . |

* cited by examiner

*Primary Examiner*—Michael G. Ambrose
(74) *Attorney, Agent, or Firm*—Noreen C. Johnson; Douglas E. Stoner

(57) ABSTRACT

An improved method for producing an aromatic carbonate by reacting an aromatic hydroxy compound, carbon monoxide and oxygen in the presence of a catalyst system comprising at least one of palladium or a palladium compound; at least one lead compound; at least one halide source; and at least one desiccant, wherein the ratio of equivalents of lead co-catalyst relative to equivalents of palladium catalyst is optimized to increase reaction rate, as well as to allow production of aromatic carbonate in an economically feasible continuous process.

14 Claims, 2 Drawing Sheets

METHOD FOR MAKING AROMATIC CARBONATES

BACKGROUND OF THE INVENTION

The present invention relates to the preparation of aromatic carbonates by carbonylation of an organic aromatic hydroxy compound, such as phenol, in the presence of a catalyst. More particularly, this invention relates to improved methods for the carbonylation of aromatic hydroxy compounds by a mixture of carbon monoxide and oxygen in the presence of a catalyst comprising palladium and a co-catalyst comprising lead.

Aromatic carbonates, such as diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents. This preparation requires economical access to large quantities of diaryl carbonates.

Various methods have been disclosed for the preparation of diaryl carbonates by the carbonylation of aromatic hydroxy compounds with carbon monoxide and oxygen in the presence of a catalyst system. The majority of the disclosures are directed to either batch-type processes, or to "batch flow" systems wherein all reactants other than gases are added to the reaction batch-wise, while gases are provided continuously throughout the reaction. As is well known, continuous flow processes are considerably more economical on a commercial scale than either batch-type or batch flow processes. There thus remains a need in the art for methods of carbonylation wherein diaryl carbonates may to produced in a continuous process in high yield.

In general, the carbonylation reaction requires a complex catalyst system, comprising at least a catalyst, a co-catalyst and a generally organic halide source. U.S. Pat. No. 4,187,242 to Chalk discloses catalysts selected from Group VIIIB metals, i.e., ruthenium, rhodium, palladium, osmium, iridium and platinum, or a complex thereof. Further developments in the carbonylation of hydroxy aromatic compounds have focused primarily on the development of the co-catalyst and other elements of the catalyst system (the "co-catalyst package"). The yield and purity of the diaryl carbonate product vary widely depending on the identity of the co-catalyst and other elements. Thus the reaction conditions which optimize the purity and yield of the diaryl carbonates are different for each co-catalyst package.

Co-catalysts generally comprise a metallic species, for example cobalt, iron, cerium, manganese, copper, or lead, and an organic compound. Thus, for example, U.S. Pat. No. 5,142,086 to King, Jr., et al. discloses metallic co-catalyst selected from cobalt, iron, cerium, manganese, molybdenum, samarium, vanadium, chromium, and copper and an organic co-catalyst selected from aromatic ketones, aliphatic ketones and aromatic polycyclic hydrocarbons. U.S. Pat. No. 5,231,210 to Joyce et al. discloses a cobalt pentacoordinate complex co-catalyst and a quaternary onium salt. U.S. Pat. No. 5,284,964 to Pressman et al. discloses an inorganic co-catalyst selected from cobalt, manganese, and copper and organic co-catalyst selected from quaternary onium salts and terpyridine. Other co-catalyst systems include a divalent or trivalent manganese salt in combination with a tetraalkylammonium halide, as disclosed in EP 350,697 to Chang; a divalent or trivalent cobalt compound, tetraalkylammonium halide and a quinone as disclosed in EP 350,700 to Chang; or a copper compound, a quinone and onium halide as disclosed in U.S. Pat. No. 5,336,803 to Kezuka et al.

One catalyst system of particular interest is disclosed in U.S. Pat. No. 5,498,789 to Takagi et al. The catalyst system consists of a palladium compound, at least one lead compound, at least one halide selected from quaternary ammonium halides and quaternary phosphonium halides, and optionally at least one copper compound. Use of a lead co-catalyst yields a process wherein the yield of aromatic carbonate per palladium (turnover number of palladium) is high, i.e. greater than about 700. However, use of a lead co-catalyst also results in a low reaction rate, too low for commercial purposes. Accordingly, there also remains a need in the art for optimization and improvement of carbonylation of aromatic hydroxy compounds in the presence of catalyst systems comprising lead co-catalysts.

SUMMARY OF THE INVENTION

The above-discussed and other drawbacks and deficiencies of the prior art are overcome or alleviated by the improved method of the present invention, comprising producing an aromatic carbonate by reacting an aromatic hydroxy compound, carbon monoxide and oxygen in the presence of a catalyst system comprising at least one palladium source; at least one lead compound; at least one halide source; and at least one desiccant, wherein the quantity of lead is optimized to increase the reaction rate, as well as to allow production of aromatic carbonate in an economically feasible continuous process.

BRIEF DESCRIPTION OF THE DRAWINGS

Referring now to the drawings wherein like elements are numbered alike in the several FIGURES.

DETAILED DESCRIPTION OF THE INVENTION

Figure 1:
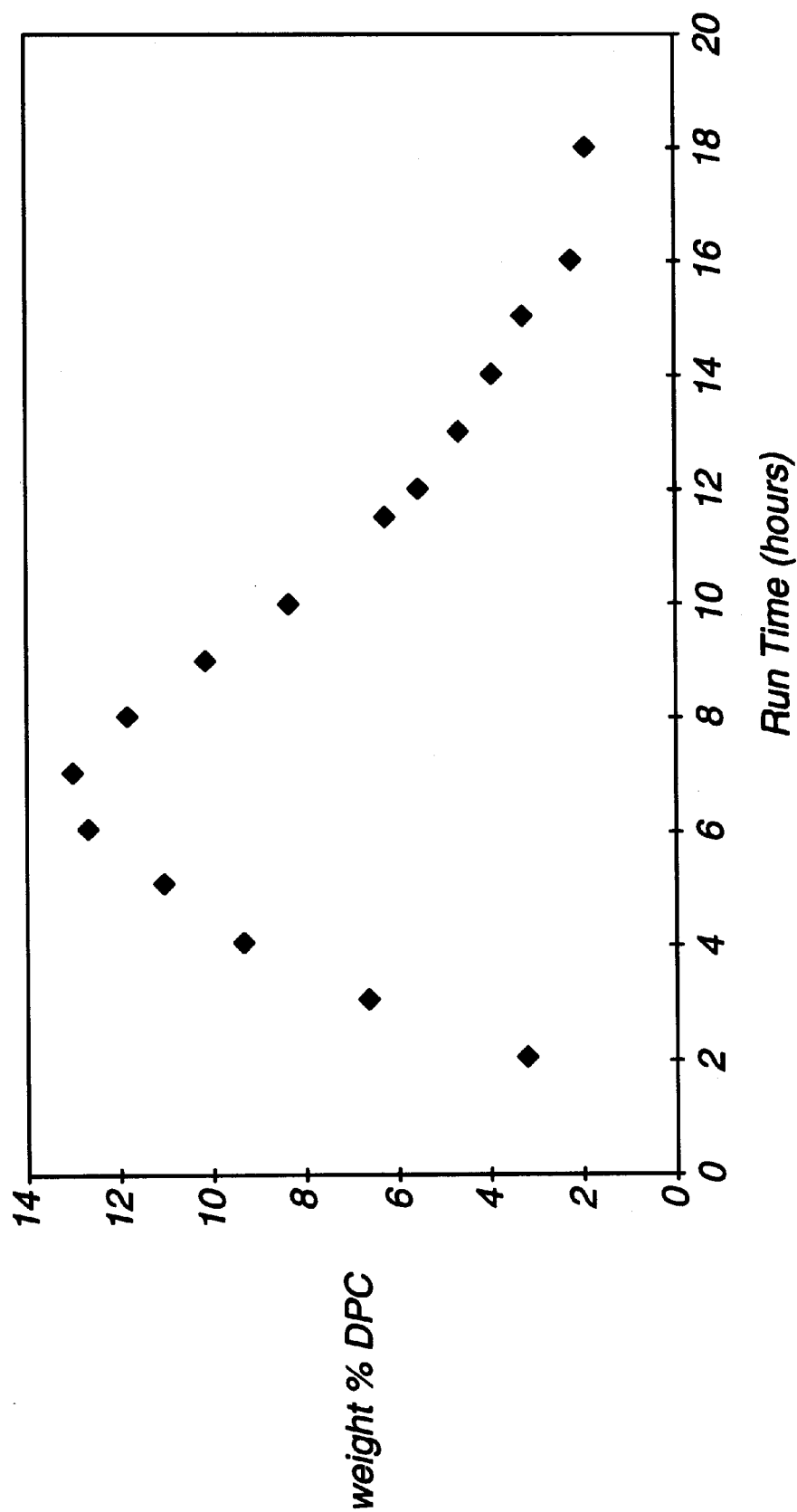
FIG. 1 is a graph showing quantity of diphenyl carbonate produced over time in a fully continuous process, wherein the catalyst comprises about 15 equivalents of PbO per equivalent of Pd (as $Pd(acac)_2$).

As mentioned above, use of a lead/halide source co-catalyst system results in a reaction wherein the turnover number of the palladium catalyst is high, especially in the presence of low quantities of palladium, e.g., 0.5 to 50 micromoles of palladium per mole of aromatic hydroxy compound. High palladium turnover numbers are economically advantageous, in that higher yields of product are available per unit of catalyst. However, despite the high palladium turnover numbers, this catalyst system is unsuitable for use in continuous processes due to the low rate of reaction. Furthermore, as is shown in FIG. 1, the percent of diphenylcarbonate produced over 18 hours decreases significantly after about 8 hours in the presence of a catalyst system comprising about 15 equivalents of lead per equivalent of palladium. Such results are inconsistent with production of diarylcarbonates by continuous processes.

One embodiment disclosed herein is an improved method of producing an aromatic carbonate by reacting an aromatic hydroxy compound, carbon monoxide, and oxygen in the presence of a catalyst system comprising at least one palladium source; at least one lead compound; at least one halide source; and at least one desiccant, which leads to improvements in the palladium turnover numbers of the reaction. Preferably, the quantity of the lead is optimized to increase the reaction rate, as well as to allow production of aromatic carbonate in an economically feasible continuous process.

Aromatic hydroxy compounds which can be used in the practice of the invention include monocyclic, polycyclic or fused polycyclic aromatic monohydroxy or polyhydroxy compounds having from 6 to 30, and preferably from 6 to 15 carbon atoms. Illustrative aromatic compounds include, but are not limited to, phenol, cresol, xylenol, resorcinol, hydroquinone, naphthol, catechol, cumenol, the various isomers of dihydroxynaphthalene, bis(4-hydroxyphenyl) propane-2,2,α,α'-bis(4-hydroxyphenyl)p-diisopropylbenzene, and bisphenol A. Aromatic monohydroxy compounds are particularly preferred, with phenol being the most preferred.

Other essential reagents in the method of this invention are oxygen and carbon monoxide, which react with the phenol to form the desired diaryl carbonate. The carbon monoxide may be high-purity carbon monoxide or carbon monoxide diluted with another gas such as nitrogen, argon, carbon dioxide or hydrogen, which have no negative effects on the reaction. The oxygen used in the present invention may be high purity oxygen, air, or oxygen diluted with another gas such as nitrogen, argon, carbon dioxide or hydrogen which have no negative effects on the reaction.

The catalyst system used in the reaction of the present invention comprises a combination system containing at least one palladium source; at least one lead compound; at least one halide source; and at least one desiccant. Examples of the at least one palladium source that can be used in the present invention include palladium or palladium compounds such as palladium black; supported palladium such as palladium/carbon, palladium/alumina, palladium/silica, and the like; inorganic palladium salts such as palladium chloride, palladium bromide, palladium iodide, palladium sulfate, palladium nitrate and the like; and organic palladium salts such as palladium acetate, palladium oxalate and the like. Palladium (II) acetylacetonate, $(Pd(acac)_2)$, palladium complexes such as $PdCl_2(PhCN)_2$, $PdCl_2(PPh_3)_2$, and others known in the art, or a mixture of palladium and a compound which can produce one or more of the above complexes in the reaction system may also be used. Mixtures of the aforementioned palladium sources are also contemplated. Palladium/carbon, palladium acetate, and $Pd(acac)_2$ are preferred.

At least one lead compound is present in the catalyst system. The lead compound is preferably soluble in a liquid phase under the reaction conditions. Examples of such lead compounds include lead oxides, for example $PbO$, $Pb_3O_4$, and $PbO_2$; lead carboxylates, for example $Pb(OC(O)CH_3)_2$, $Pb(OC(O)CH_3)_4$, and $Pb(OC(O)C_2H_5)_2$; inorganic lead salts such as $Pb(NO_3)_2$ and $PbSO_4$; alkoxy and aryloxy lead compounds such as $Pb(OCH_3)_2$, and $Pb(OC_6H_5)_2$; and lead complexes such as phthalocyanine lead and the like. Of these compounds, lead oxides and lead compounds represented by the formula $Pb(OR)_2$ wherein R is an aryl group having a carbon number from 6 to 10 are preferred. Mixtures of the aforementioned lead compounds are also contemplated.

At least one halide source is also present in the catalyst system. The halide source is preferably a quaternary ammonium halide or quaternary phosphonium halide represented by the following formula:

$R^1R^2R^3R^4NX$ or $R^1R^2R^3R^4PX$ wherein $R^1$ to $R^4$ are each independently an alkyl group or aryl group, each group independently having a carbon number of 1 to about 24, and X is halogen. Bromides are preferred, for example tetra-n-butylammonium bromide, tetraphenylphosphonium bromide and the like. Other halide sources include hexasubstituted guanidinium halides, such as hexaalkyl guanidinium halides, hexaaryl guanidinium halides, and hexasubstituted guanidinium halides containing mixtures of alkyl and aryl substituents each substituent group independently having a carbon number of 1 to 22; for example hexaalkylguanidinium chlorides or bromides. Hexaethylguanidinium bromide is preferred. Mixtures of the aforementioned halide sources are also suitable for use in the invention.

At least one desiccant is present in the catalyst system. A desiccant is preferably a non-reactive material such as a molecular sieve. 3-Angstrom (A) molecular sieves are preferred. The presence of a desiccant is particularly important over long reaction times, for example in continuous reaction processes, in order to prevent degradation of the diaryl carbonate product. As shown in Example 1 and Comparative Example 2, the presence of a desiccant such as 3 A molecular sieves can lead to about a 40% increase in the palladium turnover number, which an provide a significant economic savings for a large-scale process.

Other organic additives, for example aromatic diols (such as hydroquinone), an oxidation product thereof (such as quinone), or aromatic amines, all of which are used in conventional catalyst systems, may be added to the reaction system.

An inert solvent such as hexane, heptane, cylcohexane, benzene, toluene, xylene, methylene chloride, chloroform, chlorobenzene, diethyl ether, diphenyl ether, tetrahydrofuran, or dioxane can be used. When an aromatic hydroxy compound as a raw material is used as a reaction solvent, another solvent need not be used, although mixtures of solvents are also suitable for use in the present invention.

An effective amount of the palladium catalyst is, for example, an amount sufficient to provide about 1 mole (gram-atom) of palladium per 100 to 10,000,000 and preferably per 1000 to 1,000,000 equivalents of aromatic hydroxy compound. An effective amount of lead compound is an amount sufficient to provide about 1 mole of lead per 10 to 10,000 and preferably per 100 to 10,000 moles of aromatic hydroxy compound. An effective amount of halide source is an amount sufficient to provide about 1 to about 10,000 moles of halide source per mole of aromatic hydroxy compound.

Reaction is effected in a reactor in which the above-described aromatic hydroxy compound and catalyst system are charged under pressure of carbon monoxide and oxygen and heating. In the reaction, the absolute total pressure is within the range of about 1 to about 500 atmospheres (atm), preferably about 1 to about 150 atm. The composition ratio between carbon monoxide and oxygen is preferably beyond the explosion range of these gases from the viewpoint of safety. Gas is supplied to the reaction mixture in proportions of about 2–50 mole percent oxygen, with the balance being carbon monoxide. The gases may be introduced separately or as a mixture, to a total pressure in the range of about 10 to about 250 atmospheres. Reaction temperatures in the range of about 60–150° C. are typical. In order for the reaction to be as rapid as possible, it is preferred to substantially maintain the total gas pressure and partial pressure of carbon monoxide and oxygen, as is described in accordance with the U.S. Pat. No. 5,399,734 to King et al., until conversion of the hydroxy aromatic compound is complete.

The diaryl carbonates produced by this method may be isolated by conventional techniques. It is often preferred to form and thermally crack an adduct of the diaryl carbonate with the hydroxy aromatic compound, as is described in U.S. Pat. Nos. 5,239,106 and 5,312,955.

In an especially preferred embodiment, the inventors hereof have unexpectedly found that for a catalyst system comprising palladium or a palladium compound, a lead compound, a halide source, and a desiccant, optimization of the ratio of lead co-catalyst to palladium catalyst results in an increased turnover number for palladium. As is shown by Example 3 and comparative Example 4, a four-fold increase in the equivalents of lead oxide to equivalents of palladium results in a significant increase in palladium turnover number, from 2922 to 4167.

Figure 2:
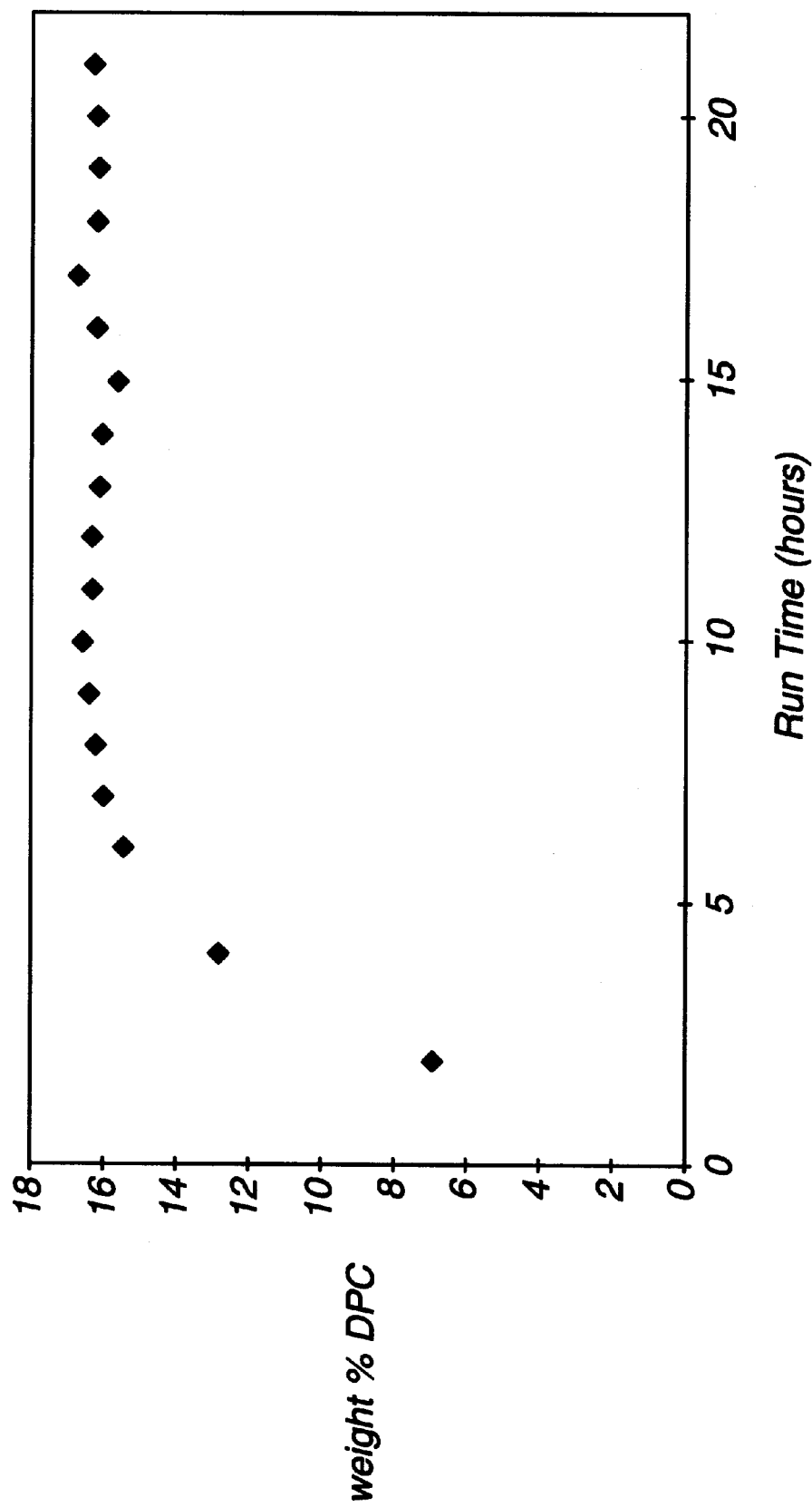
FIG. 2 is a graph showing quantity of diphenyl carbonate produced over time, also in a fully continuous process, wherein the catalyst comprises about 62 equivalents of PbO per equivalent of Pd (as $Pd(acac)_2$).

The inventors hereof have furthermore unexpectedly found that a higher ratio of lead co-catalyst to palladium catalyst is required in order to optimize yield over long reaction periods, such as are found in continuous processes. Thus, as is shown in FIG. 2, use of about 62 equivalents of lead per equivalent of palladium results in a high yield of diphenylcarbonate production for a period in excess of 18 hours. Continuous (as opposed to batch) production of diaryl carbonate using a palladium/lead catalyst system is therefore possible where a lead compound is present in an amount sufficient to provide greater than about 17 equivalents of lead per equivalent of palladium. Preferably a lead compound is present in an amount sufficient to provide between about 25 and about 100 equivalents of lead per equivalent of palladium, and most preferably between about 50 and about 70 equivalents of lead per equivalent of palladium.

The above-described embodiments are further illustrated by the following non-limiting Examples.

EXAMPLE 1

A constant composition gas flow reactor system, as disclosed in the aforementioned U.S. Pat. No. 5,399,734, was charged with 58.8837 g phenol (626 mmol), 0.0055 g Pd(acac)$_2$ (0.018 mmol), 0.2067 g PbO (0.927 mmol), 3.1982 g hexaethylguanidinium bromide (10.4 mmol) and 38 g molecular sieves (activated by drying), to yield a reaction composition having 52 equivalents of lead per equivalent of palladium and 578 equivalents of bromide source per equivalent of palladium. The reactor was sealed and heated to 100° C. with stirring, and a mixture of 9% oxygen in carbon monoxide was introduced at a flow rate of 330 mL/minute and a pressure of about 1320 psi. Gas flow was continued for 1.5 hours, after which a portion of the reaction mixture was removed and analyzed by high pressure liquid chromatography. The yield of diphenyl carbonate was 16.6 g (27 weight %). The rate of reaction was 0.84 moles of diphenyl carbonate per liter per hour at one and a half hours. The palladium turnover (moles of diphenyl carbonate produced per mole of palladium charged) was 4299. The bromide cocatalyst turnover number (moles of diphenyl carbonate produced per mole of bromide co-catalyst charged) was 7.5.

After an additional 1.5 hours of gas flow (for a total of 3 hours), a portion of the reaction mixture was removed and analyzed by high pressure liquid chromatography. The yield of diphenyl carbonate was 23.2 grams (37 weight %). The rate of reaction was 0.58 moles of diphenyl carbonate per liter per hour at three hours. The palladium turnover number was 5989. The bromide co-catalyst turnover was 10.4.

EXAMPLE 2 (COMPARATIVE)

A constant composition gas flow reactor was charged with 60.9546 g phenol (648 mmol), 0.0049 g Pd(acac)$_2$ (0.016 mmol), 0.2111 g PbO (0.947 mmol), and 3.2111 g hexaethylguanidinium bromide (10.4 mmol) in the absence of any added desiccant, to yield a reaction composition having 59 equivalents of lead per equivalent of palladium and 650 equivalents of bromide source per equivalent of palladium. The reactor was sealed and heated to 100° C. with stirring, and a mixture of 9% oxygen in carbon monoxide was introduced at a flow rate of 330 mL/minute and a pressure of about 1320 psi. Gas flow was continued for 1.5 hours, after which a portion of the reaction mixture was removed and analyzed by high pressure liquid chromatography. The yield of diphenyl carbonate was 14.8 g (23 weight %). The rate of reaction was 0.72 moles of diphenyl carbonate per liter per hour at one and a half hours. The palladium turnover number was 4302. The bromide co-catalyst turnover number was 6.6.

After an additional 1.5 hours of gas flow (for a total of 3 hours), a portion of the reaction mixture was removed and analyzed by high pressure liquid chromatography. The yield of diphenyl carbonate was 14.5 g (22.5 weight %). The rate of reaction was 0.35 moles of diphenyl carbonate per liter per hour at three hours. The palladium turnover number was 4208. The bromide co-catalyst turnover number was 6.5.

EXAMPLE 3

A constant composition gas flow reactor system was charged with 59.5839 g phenol (633 mmol), 0.0051 g Pd(acac)$_2$ (0.017 mmol), 201.2 g PbO (0.902 mmol), and 3.2062 g hexaethylguanidinium bromide (10.4 mmol), to yield a reaction composition having 53.8 equivalents of lead per equivalent of palladium and 612 equivalents of bromide source per equivalent of palladium. The reactor was sealed and heated to 100° C. with stirring, and a mixture of 9% oxygen in carbon monoxide was introduced at a flow rate of 330 mL/minute and a pressure of about 1320 psi. Gas flow was continued for 1.5 hours, after which a portion of the reaction mixture was removed and analyzed by high pressure liquid chromatography. The yield of diphenyl carbonate was 14.9 g (23.7 weight %). The rate of reaction was 0.74 moles diphenyl carbonate per liter per hour at one and a half hours. The palladium turnover number was 4174. The bromide co-catalyst turnover number was 6.7.

EXAMPLE 4 (COMPARATIVE)

A constant composition gas flow reactor system was charged with 59.2921 g phenol (630 mmol), 0.0053 g Pd(acac)$_2$ (0.0174 mmol), 53.3 g PbO (0.239 mmol), and 3.1999 g hexaethylguanidinium bromide (10.4 mmol) to yield a reaction composition having 13.7 equivalents of lead per equivalent of palladium and 598 equivalents of bromide source per equivalent of palladium. The reactor was sealed and heated to 100° C. with stirring, and a mixture of 9% oxygen in carbon monoxide was introduced at a flow rate of 330 mL/minute and a pressure of about 1320 psi. Gas flow was continued for 1.5 hours, after which a portion of the reaction mixture was removed and analyzed by high pressure liquid chromatography. The yield of diphenyl carbonate was 10.9 g (17.4 weight %). The rate of reaction was 0.54 moles diphenyl carbonate per liter per hour at one and a half hours. The palladium turnover number was 2922. The bromide co-catalyst turnover number was 4.9.

EXAMPLE 5

A phenolic solution (feedstream A) was prepared consisting of 2.5 grams Pd(acac)$_2$ (8.2 mmol), 112.8 grams PbO (505.8 mmol; 61.7 equivalents of lead per equivalent of palladium) in 16.0 liters of phenol. A second phenolic solution (feedstream B) was prepared consisting of 1767 grams hexaethylguanidinium bromide (5775 mmol) in 14.2 liters of phenol. Each feedstream was maintained at 65° C. and pumped at a rate of 0.4 liters/hour into a stirred, 1-gallon continuous reactor system maintained at 65° C. and 40 pounds per square inch gauge (psig). Once the reactor was filled, gas flow of a mixture consisting of 6% oxygen in carbon monoxide was initiated at a rate of 1200 standard liters per hour (SLPH) to achieve a pressure of 1200 psig, after which the reactor temperature was increased to 100° C. These conditions (100° C., 1200 psig, 1200 SLPH of 6% oxygen in carbon monoxide gas mixture, with stirring) were maintained for approximately 22 hours, and weight percent of diphenyl carbonate was determined by high pressure liquid chromatography over the course of the reaction. Yield of diphenyl carbonate over time is shown graphically in FIG. 2, which illustrates that high yields (approx. 16 weight %) of diphenyl carbonate are maintained after even 20 hours of reaction under continuous flow conditions.

EXAMPLE 6 (COMPARATIVE)

A phenolic solution (feedstream A) was prepared consisting of 2.5 g Pd(acac)$_2$ (8.2 mmol), 28.2 g PbO (126.4 mmol; 15.4 equivalents of lead per equivalent of palladium) and 16.0 liters of phenol. A second phenolic solution (feedstream B) was prepared consisting of 1767 g hexaethylguanidinium bromide (5775 mmol) in 14.2 liters of phenol. Each feedstream was maintained at 65° C. and pumped at a rate of 0.4 liters/hour into a stirred, 1-gallon continuous reactor system, maintained at 65° C. and 40 psig. Once the reactor was filled, gas flow of a mixture consisting of 6% oxygen in carbon monoxide was initiated at a rate of 1200 SLPH to achieve a pressure of 1200 psig, after which the reactor temperature was increased to 100° C. These conditions (100° C., 1200 psig, 1200 SLPH of 6% oxygen in carbon monoxide gas mixture, with stirring) were maintained for approximately 22 hours, and weight percent of diphenyl carbonate was determined by high pressure liquid chromatography over the course of the reaction. Yield of diphenyl carbonate over time is shown graphically in FIG. 1, which illustrates that yields of diphenyl carbonate are sharply reduced after about 8 hours of reaction under continuous flow conditions.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of producing diaryl carbonates, said method comprising reaction of an aromatic hydroxy compound, carbon monoxide, and oxygen in the presence of an effective quantity of a catalyst system comprising at least one palladium source; at least one lead compound, wherein the ratio of equivalents of lead to equivalents of palladium is greater than about 17; at least one halide; and at least one desiccant.

2. The method of claim 1, wherein the at least one palladium source is selected from the group consisting of palladium, palladium black, supported palladium, palladium/carbon, palladium/alumina, palladium/silica, inorganic palladium salts,. palladium chloride, palladium bromide, palladium iodide, palladium sulfate, palladium nitrate, organic palladium salts, palladium acetate, palladium oxalate, palladium (II) acetylacetonate, palladium complexes, PdCl$_2$(PhCN)$_2$, and PdCl$_2$(PPh$_3$)$_2$.

3. The method of claim 2, wherein the at least one palladium source is Pd(acac)$_2$ or palladium on carbon.

4. The method of claim 1, wherein the at least one lead compound is selected from the group consisting of lead oxides, PbO, Pb$_3$O$_4$, PbO$_2$, organic acid salts of lead, Pb(OC(O)CH$_3$)$_2$, Pb(OC(O)CH$_3$)$_4$, Pb(OC(O)C$_2$H$_5$)$_2$, lead salts, Pb(NO$_3$)$_2$, PbSO$_4$, alkoxy lead compounds, aryloxy lead compounds, Pb(OC$_6$H$_5$), Pb(OCH$_3$)$_2$, lead complexes and phthalocyanine lead complexes.

5. The method of claim 4, wherein the at least one lead compound is a lead oxide or an aryloxy lead compound.

6. The method of claim 1, wherein the at least one halide source is selected from the group consisting of quaternary ammonium halides, represented by the formula R$^1$R$^2$R$^3$R$^4$NX, wherein R$^1$ to R$^4$ are each independently an alkyl group or aryl group, each group independently having a carbon number of 1 to about 24, and X is halogen; quaternary phosphonium halides represented by the formula R$^1$R$^2$R$^3$R$^4$PX wherein R$^1$ to R$^4$ are each independently an alkyl group or aryl group, each group independently having a carbon number of 1 to about 24, and X is halogen; hexasubstituted guanidinium halides, such as hexaalkyl guanidinium halides, hexaaryl guanidinium halides, and hexasubstituted guanidinium halides containing mixtures of alkyl and aryl substituents each substituent independently having a carbon number of 1 to 22; tetra-n-butylammonium bromide, tetraphenylphosphonium bromide, and hexaethylguanidinium bromide.

7. The method of claim 6, wherein the at least one halide source is a hexaalkylguanidinium chloride or bromide.

8. The method of claim 1, wherein the at least one desiccant is a molecular sieve.

9. The method of claim 1, wherein the ratio of equivalents of lead to equivalents of palladium is between about 25 and about 100.

10. The method of claim 1, wherein the ratio of equivalents of lead to equivalents of palladium is between about 50 and about 70.

11. The method of claim 1, wherein the aromatic hydroxy compound is selected from the group consisting of monocyclic aromatic monohydroxy compounds, polycyclic aromatic monohydroxy compounds, fused polycyclic aromatic monohydroxy compounds, monocyclic aromatic polyhydroxy compounds, polycyclic aromatic polyhydroxy compounds, fused polycyclic aromatic polyhydroxy compounds, phenol, cresol, xylenol, resorcinol, hydroquinone, naphthol, catechol, cumenol, isomers of dihydroxynaphthalene, bis(4-hydroxyphenyl)propane-2,2, α,α'-bis(4-hydroxyphenyl)p-diisopropylbenzene, and bisphenol A.

12. The method of claim 11, wherein the aromatic hydroxy compound is phenol.

13. The method of claim 4, wherein the lead compound is a lead oxide or Pb(OR)$_2$, wherein R is an aryl group having from 6 to 10 carbons.

14. The method of claim 1, wherein the diaryl carbonate is produced in a continuous process.

* * * * *